(12) United States Patent
Okumura et al.

(10) Patent No.: US 7,758,736 B2
(45) Date of Patent: Jul. 20, 2010

(54) GAS SENSOR

(75) Inventors: Tatsuya Okumura, Gifu (JP); Satoshi Ishikawa, Gifu (JP); Takehiro Oba, Gifu (JP); Tomohiko Funahashi, Gifu (JP)

(73) Assignee: NGK Spark Plug Co., Ltd., Aichi (JP)

( * ) Notice: Subject to any disclaimer, the term of this patent is extended or adjusted under 35 U.S.C. 154(b) by 324 days.

(21) Appl. No.: 11/892,718

(22) Filed: Aug. 27, 2007

(65) Prior Publication Data

US 2008/0067066 A1    Mar. 20, 2008

(30) Foreign Application Priority Data

Sep. 14, 2006   (JP) .............................. 2006-250097
Apr. 24, 2007   (JP) .............................. 2007-114357

(51) Int. Cl.
*G01N 27/407*    (2006.01)

(52) U.S. Cl. ........................... 204/428; 204/424

(58) Field of Classification Search ................ 204/424, 204/428; 205/784; 73/23.31, 23.32
See application file for complete search history.

(56) References Cited

U.S. PATENT DOCUMENTS 5,846,391 A * 12/1998 Friese et al. ................ 204/424

2002/0053233 A1   5/2002 Grieser et al.
2004/0144645 A1 * 7/2004 Yamada et al. .............. 204/424
2005/0241937 A1  11/2005 Shichida et al.

FOREIGN PATENT DOCUMENTS

JP           2001-74686 A        3/2001

* cited by examiner

*Primary Examiner*—Kaj K Olsen
(74) *Attorney, Agent, or Firm*—Sughrue Mion, PLLC (57) ABSTRACT

A detecting element (10) of a gas sensor (1) is held with a detecting portion (11) projecting from a front-end engaging-portion (56) of a metallic shell (50) and is accommodated for protection in an inner protector (120) in a gas detection chamber (129). Exhaust gas introduced into the gas detection chamber (129) is exhausted through an exhaust hole (160). The exhaust hole is formed by cutting off a portion of a side wall (127) of a recess portion (125), which is formed by pressing inward a portion between two slits formed in a front end wall (124). A bottom wall (126) of the recess portion (125) is located frontward of the detecting element (10) with respect to the direction of an axis O, thereby preventing a water droplet which comes flying from the outside from directly contacting the detecting element (10).

12 Claims, 6 Drawing Sheets

GAS SENSOR

BACKGROUND OF THE INVENTION

1. Field of the Invention

The present invention relates to a gas sensor having a protector for protecting, a detecting element exposed to exhaust gas from contact with adhering water droplets.

2. Description of the Related Art

Conventionally, a gas sensor is known having a detecting element in which electromotive force is generated in a magnitude corresponding to the concentration of a specific gas; for example, $NO_x$ (nitrogen oxides) or oxygen, contained in exhaust gas of an automobile or the like, or whose resistance varies with the concentration. The gas sensor is attached to an exhaust pipe of an automobile, or the like. Since the detecting element is exposed to exhaust gas of high temperature, subjecting the detecting element to thermal shock caused by water contained in exhaust gas and adhering to the detecting element may crack or break the detecting element. In order to cope with this problem, the gas sensor is fitted with a protector for covering the detecting element, thereby protecting the detecting element from contact with adhering water droplets (refer to, for example, Patent Document 1).

The protector of the gas sensor of Patent Document 1 has a dual structure consisting of an inner protector (inner tubular member) which covers a front end portion of the detecting element projecting from a metallic shell, and an outer protector (outer tubular member) which radially encloses the inner protector so as to form a clearance present between the inner protector and the outer protector. Exhaust gas is introduced into the clearance between the outer protector and the inner protector through outer introduction holes (outer-wall gas introduction holes) formed in the outer protector. The exhaust gas is then introduced into the inner protector through inner introduction holes (inner-wall gas introduction holes) formed in the inner protector, to thereby contact the detecting element.

A front end portion of the inner protector of the gas sensor of Patent Document 1 is tapered and projects from a front end of the outer protector. An exhaust hole is formed in a front end of the inner protector. When exhaust gas flowing outside the gas sensor contacts the taper, a gas flow along the taper is generated, to thereby generate a negative pressure (suction) in the vicinity of the exhaust hole. By virtue of the suction, exhaust gas which has been introduced into the inner protector is promptly discharged through the exhaust hole. Particularly, gas flow along the taper generates suction around a portion of the inner protector and a portion of the outer protector located in the vicinity of the exhaust hole.

[Patent Document 1] Japanese Patent Application Laid-Open (kokai) No. 2004-109125

3. Problems to be Solved by the Invention

However, in the gas sensor of Patent Document 1, the exhaust hole of the inner protector is sized to ensure discharge of exhaust gas. Thus, in some cases, a water droplet or the like could enter the inner protector through the larger-sized exhaust hole. Since a front end portion of the detecting element is directly visible from the outside, a water droplet which enters through the exhaust port may adhere to the detecting element. If the detecting element is subjected to thermal shock caused by an adhering water droplet, the detecting element may crack or break.

SUMMARY OF THE INVENTION

The present invention has been made in view of the above-noted problems of the prior art, and an object thereof is to provide a gas sensor having a protector which can effectively protect a detecting element from contact with adhering water droplets while maintaining good gas discharge.

The above object has been achieved in a first aspect (1) by providing a gas sensor comprising a detecting element which extends in an axial direction and has a detecting portion at a front end portion thereof, the detecting portion detecting a specific gas component contained in a gas-to-be-measured; a housing which holds and radially encloses the detecting element, the detecting portion of the detecting element projecting from a front end portion of the housing; an inner protector which has a circumferential wall, said inner protector having a front end wall located on a front side of the circumferential wall and a rear, open end portion fixed to a front end portion of the housing so as to accommodate the detecting portion of the detecting element in the inner protector, and which inner protector has an inner introduction hole formed in its circumferential wall for introducing the gas-to-be-measured into the inner protector; and an outer protector which assumes a cylindrical shape enclosing the circumferential wall of the inner protector, such that a clearance is present between the inner protector and the outer protector, and which outer protector has an outer introduction hole formed in a circumferential wall of the outer protector for introducing the gas-to-be-measured into the clearance.

In the gas sensor according to the first aspect (1), at least either the inner protector or the outer protector has a taper portion formed on a front end side of its circumferential wall and reducing frontward in outside diameter. The front end wall of the inner protector includes a recess portion which has a bottom wall located closer to the detecting element than the front end wall, a side wall connecting the front end wall and the bottom wall, and an exhaust hole formed in the side wall and adapted to exhaust the gas-to-be-measured.

In a gas sensor according to a second aspect (2), in addition to the configuration of the invention according to (1) above, the circumferential wall of the inner protector has a drain hole located frontward of the inner introduction hole for introducing into the inner protector a water droplet which has entered the clearance, and the exhaust hole of the recess portion is located frontward of a rear end of the drain hole.

In a gas sensor according to a third aspect (3), in addition to the configuration of the invention according to (1) or (2) above, the detecting element assumes the form of a plate, and the exhaust hole does not overlap the detecting element in the axial direction.

In a gas sensor according to a fourth aspect (4), in addition to the configuration of the invention according to any one of (1) to (3) above, the exhaust hole is opened in the form of a through-hole in each of two facing regions of the side wall of the recess portion.

In a gas sensor according to a fifth aspect (5), in addition to the configuration of the invention according to (4) above, the detecting element assumes the form of a plate, and the inner protector is fixed to the housing such that a facing direction of the two exhaust holes of the recess portion coincides with a thickness direction of the detecting element held by the housing.

In a gas sensor according to a sixth aspect (6), in addition to the configuration of the invention according to any one of (1) to (5) above, the recess portion is located frontward of a rear end of the taper portion.

In a gas sensor according to a seventh embodiment (7), in addition to the configuration of the invention according to any one of (1) to (6) above, the exhaust hole has an opening which has a trapezoidal shape such that a front end width of the opening is greater than a rear end width of the opening.

In a gas sensor according to an eighth aspect (8), in addition to the configuration of the invention according to any one of (1) to (7) above, the drain hole is located frontward of a rear end of the outer introduction hole of the outer protector, and a front end of the detecting element is located rearward of the rear end of the outer introduction hole of the outer protector.

In a gas sensor according to a ninth aspect (9), in addition to the configuration of the invention according to any one of (1) to (8) above, the taper portion is present on the inner protector, and the inner protector projects from a front end of the outer protector such that the bottom wall of the recess portion is located frontward of the front end of the outer protector.

EFFECT OF THE INVENTION

In the gas sensor of the invention according to (1) above, the exhaust hole is not opened directly in the front end wall of the inner protector, but is opened in the side wall of the recess portion. Thus, the interior and the exterior of the inner protector are unlikely to communicate with one another along the axial direction. That is, the detecting portion of the detecting element accommodated within the inner protector is obstructed, in the axial direction, by the front end wall of the inner protector and by a bottom portion of a wall of the recess portion, where a peripheral edge of the bottom portion (hereinafter, called a "bottom wall") is surrounded by the side wall. Accordingly, the detecting portion of the detecting element is unlikely to be directly exposed to the exterior of the gas sensor. By virtue of this configuration, even when a water droplet or the like enters the recess portion from outside the inner protector along the axial direction, the water droplet is obstructed by the bottom wall and is thus unlikely to reach the detecting element. Therefore, the detecting element can be protected from contact with adhering water droplets. Since there is no need to cover the entire inner protector (particularly the front end wall of the inner protector) with the outer protector for protection against contact with adhering water droplets, both of the inner and outer protectors can be reduced in size, and, accordingly, the gas sensor can be reduced in size.

A water droplet which has entered the clearance between the outer protector and the inner protector is introduced into the inner protector through the drain hole. According to the invention of (2) above, the exhaust hole is located frontward of a rear end of the drain hole in the axial direction. That is, with respect to a flow path of exhaust gas flowing in the outer and inner protectors, the exhaust hole is located downstream of the drain hole. This prevents backward entry of a water droplet which has been introduced into the inner protector, into the clearance between the outer protector and the inner protector through the drain hole, thereby preventing water from remaining in the protector. Therefore, drainage from inside the inner protector is enhanced, and, accordingly, the detecting element can be protected from contact with adhering water droplets.

Meanwhile, in the case where a water droplet enters the recess portion along a direction different from the axial direction, the water droplet may reach the interior of the inner protector. According to the invention of (3) above, the exhaust hole does not overlap the detecting element in the axial direction. Thus, the detecting element is not located on a straight line which extends between the interior and the exterior of the inner protector through the exhaust hole. By virtue of this configuration, even when a water droplet enters the recess portion from outside of the inner protector along a direction different from the axial direction and then enters the inner protector through the exhaust hole, the water droplet does not come in contact with the detecting element. Therefore, the detecting element can be protected from contact with adhering water droplets.

According to the invention of (4) above, the exhaust hole is opened in each of two facing regions of the side wall of the recess portion, whereby the opening area of the exhaust hole can be increased without the need to increase the areal percentage of the recess portion to the front end wall. Furthermore, the opening area of the exhaust hole can be increased without the need to increase the depth of the recess portion. Thus, this configuration can enhance exhaust-gas exhaustibility and water-droplet drainage from the exhaust hole of the inner protector. These exhaust holes can be readily formed, for example, by forming two parallel slits in the front end wall and then pressing a portion between the two slits into the inner protector. Consequently, manufacturing labor can be reduced, and manufacturing costs can be lowered.

According to the invention of (5) above, the inner protector is fixed to the housing such that a facing direction of the two exhaust holes of the recess portion coincides with a thickness direction of the detecting element held by the housing. Thus, the opposite ends of the detecting element with respect to a width direction of the detecting element are not located on a straight line which extends between the interior and the exterior of the inner protector through the exhaust hole. By virtue of this configuration, even when a water droplet enters the recess portion from the outside of the inner protector along a direction different from the axial direction and then enters the inner protector, the water droplet does not come in contact with the detecting element. Therefore, the detecting element can be protected from contact with adhering water droplets.

According to the invention of (6) above, the recess portion is located frontward of a rear end of the taper portion, thereby increasing the distance between the bottom wall of the recess portion and the front end of the detecting element with respect to the axial direction. Thus, even when a portion of water droplets having entered the recess portion and having collided with the bottom wall pass through the exhaust hole and enter the inner protector, such a water splash is unlikely to reach the detecting element. Therefore, the detecting element can be protected from contact with adhering water droplets.

According to the invention of (7) above, each of the exhaust holes has a trapezoidal opening, whereby the opening area of each exhaust hole can be increased. Also, the opening area of each exhaust hole can be increased without the need to increase the depth of the recess portion. Thus, this configuration can enhance exhaust-gas exhaustibility and water-droplet drainage from the exhaust hole of the inner protector.

According to the invention of (8) above, the front end of the detecting element is located rearward of the rear end of the outer introduction hole of the outer protector, and the drain hole of the inner protector is located frontward of the rear end of the outer introduction hole. Thus, in a case where a water droplet or the like which flies toward the circumferential wall of the outer protector from the outside enters the outer protector through the outer introduction hole and directly passes through the drain hole of the inner protector to thereby enter the inner protector, the front end of the detecting element is not located in a direction of entry of the water droplet or the like. Accordingly, a water droplet or the like which has come flying from the outside does not come in direct contact with the detecting element and is drained to the exterior of the gas sensor through the exhaust hole, so that the detecting element can be protected from contact with adhering water droplets.

According to the invention of (9) above, the taper portion is provided on the inner protector, and the inner protector projects from the front end of the outer protector such that the recess portion is located frontward of the front end of the outer protector. By virtue of this configuration, the exhaust hole of the inner protector is located furthest downstream with respect to a flow path of exhaust gas and water droplets which flow in the outer and inner protectors. Therefore, exhaust-gas exhaustibility and water-droplet drainage from the exhaust hole can be further enhanced.

BRIEF DESCRIPTION OF THE DRAWINGS

FIG. 2 includes views showing the structure of a protector 100 of the gas sensor 1, wherein

FIG. 3 includes views showing the structure of the protector 100 of the gas sensor 1, wherein

FIG. 4 includes views showing the structure of an inner protector 220 of a gas sensor 200 as a variant of the gas sensor 1, wherein

DESCRIPTION OF REFERENCE NUMERALS

Reference numerals used to identify various structural features in the drawings include the following:

1, 200, 350: gas sensor
10: detecting element
50: metallic shell
56: front-end engaging-portion
100: protector
110, 310: outer protector
112: circumferential wall
115: outer introduction hole
119: gas separation chamber
120, 220, 320: inner protector
121: open end portion
122, 322: circumferential wall
123, 313: taper portion
124, 224, 324: front end wall
125, 225, 325: recess portion
126, 226: bottom wall
127, 227: side wall
129, 229: gas detection chamber
130: inner introduction hole
150: drain hole
160, 260: exhaust hole

DETAILED DESCRIPTION OF THE PREFERRED EMBODIMENTS

A gas sensor according to an embodiment of the present invention will next be described with reference to the drawings. However, the present invention should not be construed as being limited thereto.

Figure 1:
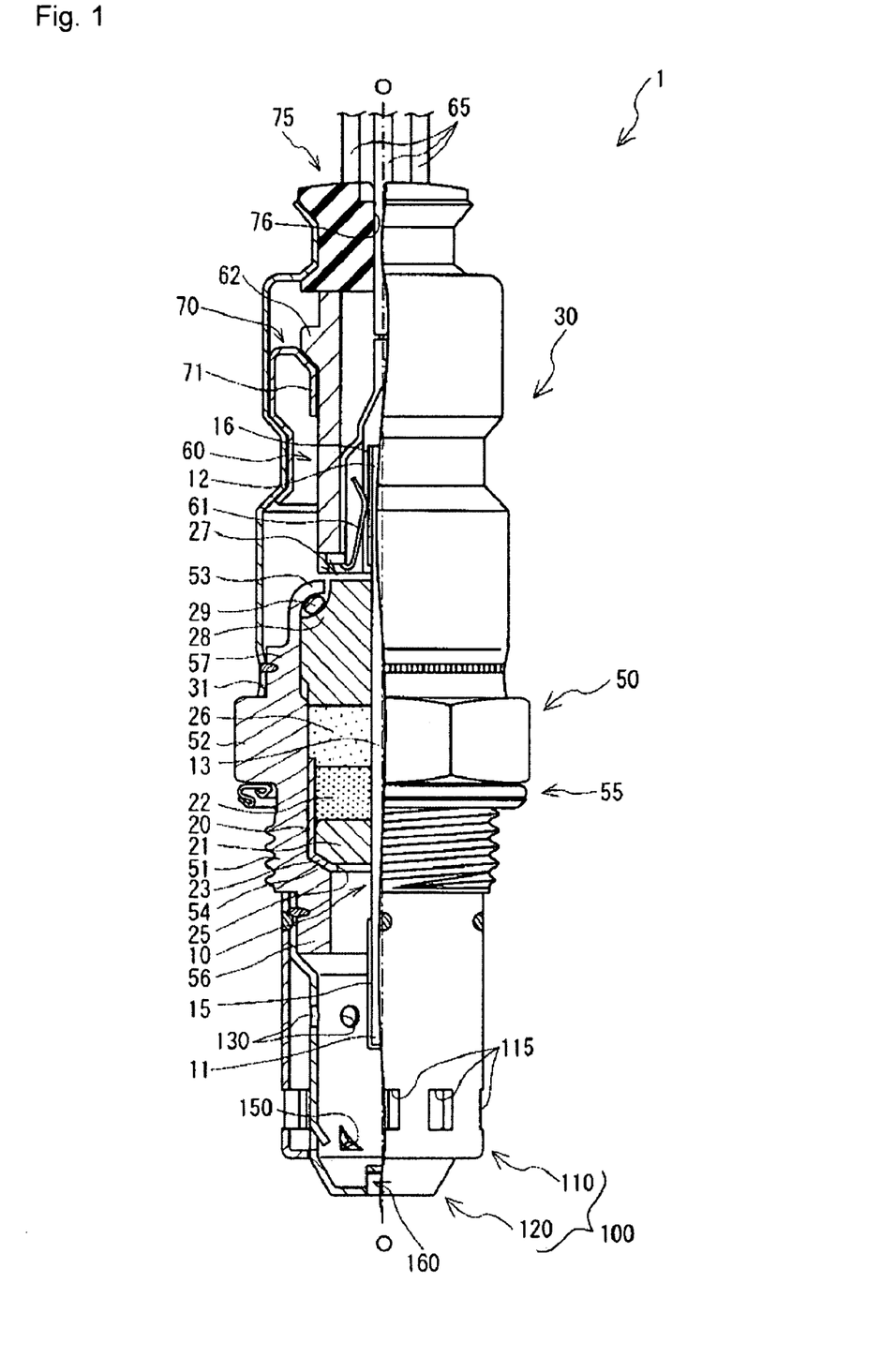
FIG. 1 is a partial sectional view of a gas sensor 1.
Figure 2A:
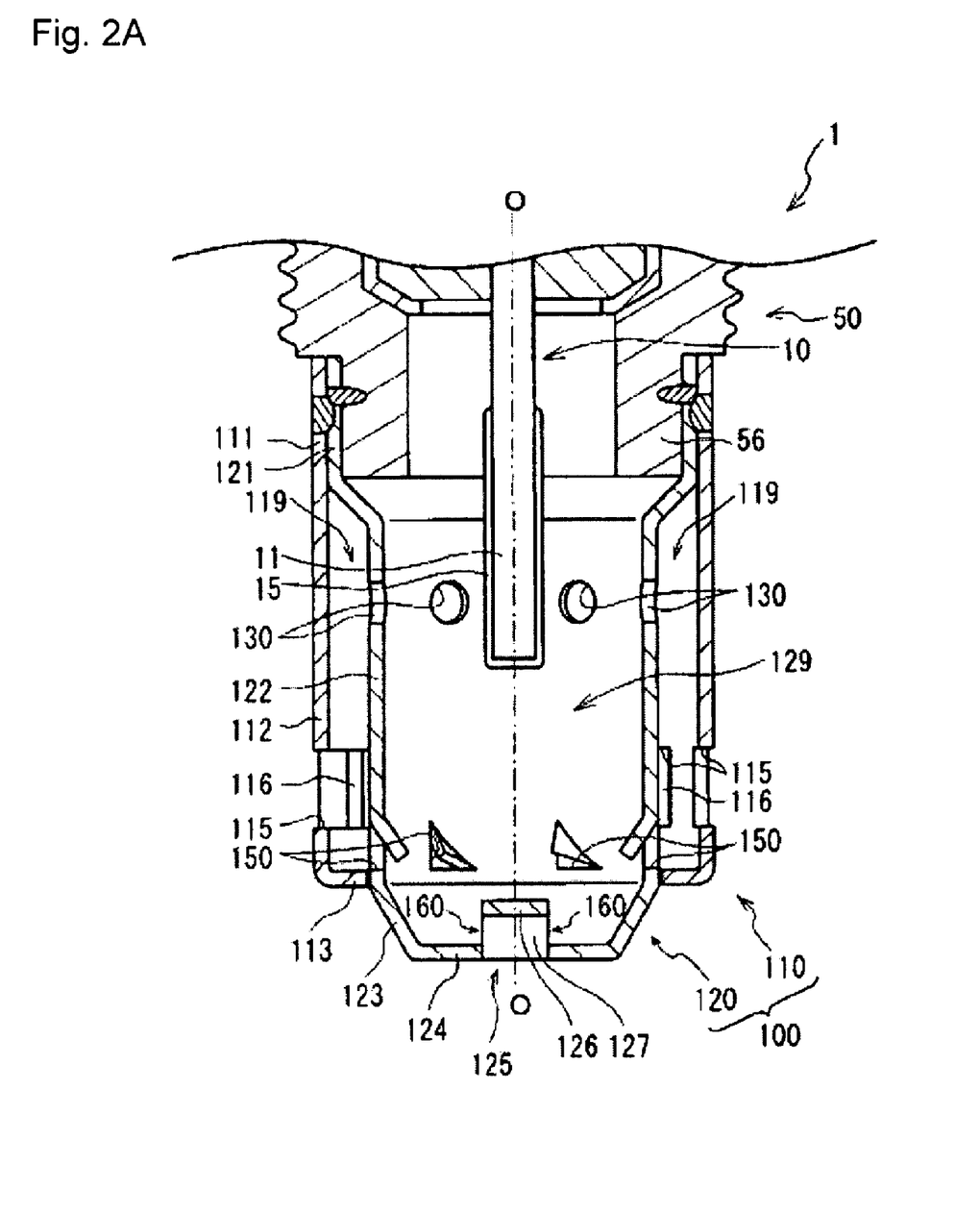
FIG. 2A is a lateral view.
Figure 2B:
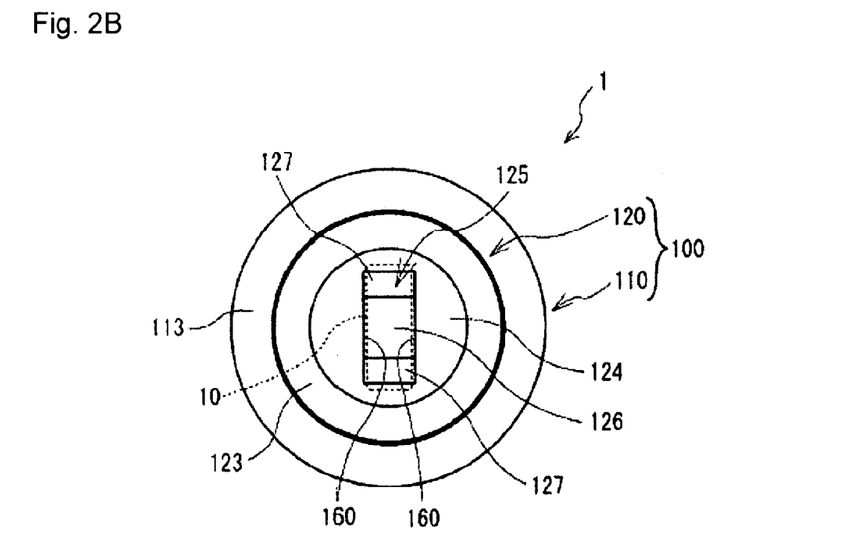
FIG. 2B is a view from a front-end side.
Figure 3A:
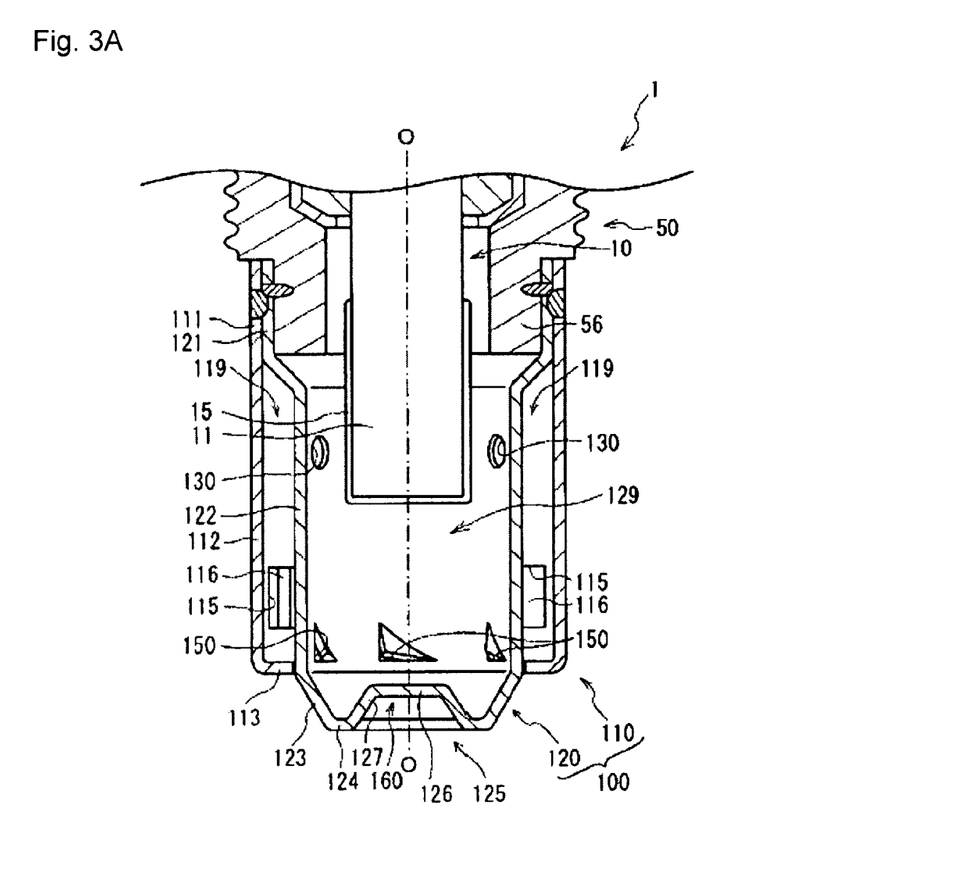
FIG. 3A is a lateral view corresponding to FIG. 2A
Figure 3B:
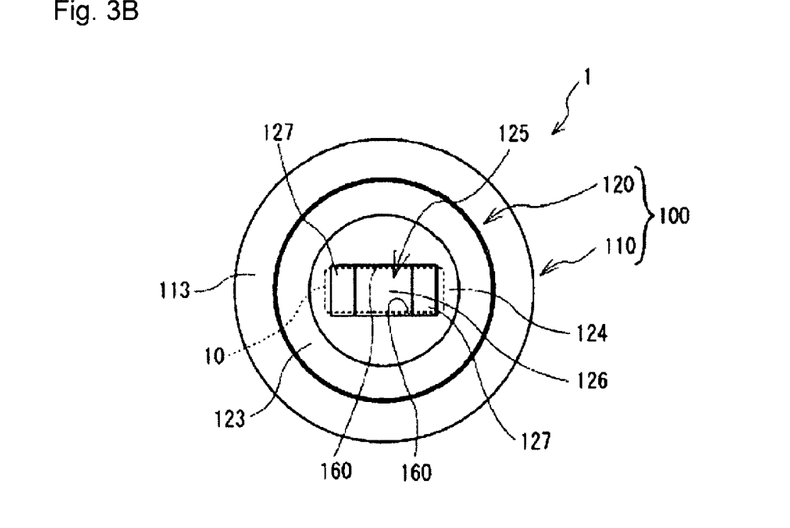
FIG. 3B is a view from the front-end side.

First, the structure of a gas sensor 1 will be described, by way of example, with reference to FIGS. 1 to 3. FIG. 1 is a partial sectional view of the gas sensor 1. FIG. 2 shows the structure of a protector 100 of the gas sensor 1, wherein FIG. 2A is a lateral view, and FIG. 2B is a view from a front-end side. FIG. 3 shows the structure of the protector 100 of the gas sensor 1, wherein FIG. 3A is a lateral view corresponding to FIG. 2A, and FIG. 2B is a view from the front-end side. Notably, in FIGS. 1 to 3, the direction of an axis O (represented by a dash-dot line) of the gas sensor 1 coincides with the vertical direction. In the following description, a side toward a detecting portion 11 of a detecting element 10 held in the gas sensor 1 is referred to as a front-end side of the gas sensor 1, and a side toward a rear end portion 12 is referred to as a rear-end side of the gas sensor 1.

The gas sensor 1 shown in FIG. 1 is attached to an exhaust pipe of an automobile (not shown). The detecting portion 11 of the detecting element 10 held in the gas sensor 1 is exposed to exhaust gas which flows through the exhaust pipe, for detecting the air/fuel ratio of the exhaust gas based on the oxygen concentration of the exhaust gas; i.e., the gas sensor 1 is a so-called full-range air/fuel ratio sensor.

As well known in this field of art, the detecting element 10 assumes the form of a plate extending in the direction of the axis O and is a generally rectangular columnar laminate in which a gas-detecting element for detecting an oxygen concentration and a heater element for promptly activating the gas-detecting element through application of heat are laminated together (a left-right direction on the paper on which FIG. 1 appears coincides with a thickness direction of the detecting element 10, and a direction perpendicular to the paper coincides with a width direction of the detecting element 10). The gas-detecting element is composed of a solid electrolyte body (not shown) which predominantly contains zirconia, and detecting electrodes (not shown) which predominantly contain platinum. The detecting electrodes are disposed at the detecting portion 11 located at the front end of the detecting element 10. In order to protect the detecting electrodes from poisoning by exhaust gas, the detecting portion 11 of the detecting element 10 is covered with a protection layer 15. The rear end portion 12 of the detecting element 10 has five electrode pads 16 (one of which is shown in FIG. 1) for allowing external connection with electrodes extending from the gas-detecting element and from the heater element. Notably, in the description of the present embodiment, the detecting element 10 corresponds to the "detecting element" in the present invention. However, strictly speaking, the detecting element does not necessarily include a heater element.

A closed-bottomed tubular metal cup 20 is disposed slightly frontward of the axial center of a trunk portion 13 of the detecting element 10 in such manner that the detecting element 10 is inserted through the interior of the metal cup 20 with the detecting portion 11 projecting from an opening 25 formed in a bottom of the metal cup 20. The metal cup 20 is a member for holding the detecting element 10 in a metallic shell 50. A front-end peripheral-portion 23 located at a peripheral portion of the bottom of the metal cup 20 is tapered toward a tubular wall portion of the metal cup 20. The metal cup 20 contains a ceramic ring 21 made of alumina and a talc ring 22 formed by compacting a talc powder, in such manner that the detecting element 10 is inserted through the ceramic ring 21 and through the talc ring 22. The talc ring 22 is crushed within the metal cup 20 so as to tightly fill an associated space, thereby holding the detecting element 10 in position within the metal cup 20.

An assembly consisting of the metal cup 20 and the detecting element 10 is circumferentially enclosed and held by the tubular metallic shell 50. The metallic shell 50 is adapted to fixedly attach the gas sensor 1 to an exhaust pipe of an automobile (not shown). The metallic shell 50 is formed from a low-carbon steel such as SUS430 and has an externally threaded portion 51 which is formed on an outer circumferential surface of the metallic shell 50 and located on a side toward the front end of the metallic shell 50. The metallic shell 50 has a front-end engaging-portion 56 which is located frontward of the externally threaded portion 51 and engaged with a protector 100, which will be described below. The metallic shell 50 also has a tool engagement portion 52 which is formed at an axially central portion of an outer circumferential surface of the metallic shell 50 for engaging a mounting tool. In order to prevent gas leakage after the gas sensor 1 is attached to the exhaust pipe, a gasket 55 is fitted to a portion of the metallic shell 50 between the front end face of the tool engagement portion 52 and the rear end of the externally threaded portion 51. The metallic shell 50 further has a rear-end engaging-portion 57 which is located rearward of the tool engagement portion 52 and with which a sheath 30 to be described below is engaged, and a crimp portion 53 which is located rearward of the rear-end engaging-portion 57 and adapted to crimp-hold the detecting element 10 in the metallic shell 50. Notably, the metallic shell 50 corresponds to the "housing" in the present invention.

The metallic shell 50 has a stepped portion 54 on its inner circumferential surface at a position substantially corresponding to the externally threaded portion 51. The front-end peripheral-portion 23 of the metal cup 20 which holds the detecting element 10 is engaged with the stepped portion 54. Furthermore, a talc ring 26 is placed in the metallic shell 50 along the inner circumference of the metallic shell 50 from the rear side of the metal cup 20 a state such that the detecting element 10 is inserted through the talc ring 26. A tubular sleeve 27 is fitted into the metallic shell 50 in such manner as to press the talc ring 26 from the rear side of the talc ring 26. The sleeve 27 has a step-like shoulder portion 28 formed on the outer circumferential surface of a rear end portion of the sleeve 27. An annular crimp packing 29 is disposed on the shoulder portion 28. In this condition, the crimp portion 53 of the metallic shell 50 is crimped in such manner as to press the shoulder portion 28 of the sleeve 27 frontward via the crimp packing 29. Being pressed by the sleeve 27, the talc ring 26 is crushed within the metallic shell 50, thereby tightly filling an associated space. By means of the talc ring 26 and the talc ring 22, which is previously placed in the metal cup 20, the metal cup 20 and the detecting element 10 are held in position within the metallic shell 50. Airtightness within the metallic shell 50 is maintained by means of the crimp packing 29 intervening between the crimp portion 53 and the shoulder portion 28 of the sleeve 27, thereby preventing outflow of combustion gas.

The rear end portion 12 of the detecting element 10 projects rearward beyond the rear end (crimp portion 53) of the metallic shell 50. The rear end portion 12 is covered with a tubular separator 60 formed from an insulating ceramic. The separator 60 internally holds the five electrode pads 16 formed on the rear end portion 12 of the detecting element 10 and five connection terminals 61 (one of which is shown in FIG. 1), which are electrically connected to the respective electrode pads 16. Also, the separator 60 protectively accommodates connections between the connection terminals 61 and corresponding five lead wires 65 (three of which are shown in FIG. 1), which extend to the exterior of the gas sensor 1.

The tubular sheath 30 is disposed in such manner as to circumferentially enclose the rear end portion 12 of the detecting element 10 to which the separator 60 is fitted. The sheath 30 is made of stainless steel (e.g., SUS304). A front open end 31 of the sheath 30 is engaged with the outer circumference of the rear-end engaging-portion 57 of the metallic shell 50. The open end 31 is crimped radially inward, and laser welding is performed on the open end 31 along the outer circumference of the open end 31, whereby the open end 31 is joined to the rear-end engaging-portion 57. The sheath 30 and the metallic shell 50 are thus united.

A tubular metal holder 70 is disposed in the clearance between the sheath 30 and the separator 60. The metal holder 70 has a support portion 71, which is formed by inwardly bending a rear end of the metal holder 70. The separator 60 is inserted through the metal holder 70 such that a flange portion 62 formed on the outer circumference of a rear end portion of the separator 60 is engaged with the support portion 71, whereby the separator 60 is supported by the support portion 71. In this condition, a portion of the sheath 30 where the metal holder 70 is disposed is crimped radially inward, whereby the metal holder 70 which supports the separator 60 is fixed to the sheath 30.

A grommet 75 made of a fluorine-containing rubber is fitted into a rear end opening of the sheath 30. The grommet 75 has five insertion holes 76 (one of which is shown in FIG. 1). The five lead wires 65 extending outwardly from the separator 60 are airtightly inserted through the respective insertion holes 76. In this condition, a portion of the sheath 30 which corresponds to the grommet 75 is crimped radially inward, whereby the grommet 75 is fixed to the rear end of the sheath 30 while pressing the separator 60 frontward.

While the detecting element 10 is held in the metallic shell 50, the detecting portion 11 of the detecting element 10 projects from a front end portion (front-end engaging-portion 56) of the metallic shell 50. The protector 100 is fitted to and fixed, by spot welding and laser welding, to the front-end engaging-portion 56 for the purpose of protecting the detecting portion 11 of the detecting element 10 from breakage or the like which could otherwise result from contamination with deposits (poisonous adhering substances such as fuel ash and oil component) contained in exhaust gas and contact with adhering water droplets. The protector 100 will next be described with reference to FIGS. 2 and 3.

As shown in FIGS. 2A, 2B, 3A and 3B, the protector 100 has a dual-structure consisting of an inner protector 120 and an outer protector 110. The inner protector 120 assumes a closed-bottomed tubular form having a front end wall 124 and a circumferential wall 122 and has a plurality of holes formed in the circumferential wall 122. The outer protector 110 assumes a tubular form so as to circumferentially enclose the inner protector 120 with a clearance (hereinafter, also called a "gas separation chamber") formed between an outer circumferential surface of the inner protector 120 and an inner circumferential surface of the outer protector 110, and has a plurality of holes formed in a circumferential wall 112. The front end wall 124 of the inner protector is exposed and not covered by the outer protector 110.

The inner protector 120 has an outside diameter that is smaller than the front-end engaging-portion 56 of the metallic shell 50. An open end portion 121 associated with an open end (rear end) of the inner protector 120 is expanded in diameter so as to externally engage the front-end engaging-portion 56. The open end portion 121 is subjected to laser welding which is externally carried out along the entire circumference of the open end portion 121, whereby the inner protector 120 is fixed to the front-end engaging-portion 56 of the metallic shell 50. A taper portion 123 is formed on the front end side of the circumferential wall 122 and in such manner as to reduce in diameter toward the front end wall 124. The circumferential wall 122 of the inner protector 120 has a plurality of (six in the present embodiment) inner introduction holes 130 which are arranged circumferentially at a position located toward the open end portion 121 with respect to the direction of the axis O. The inner introduction holes 130 are adapted to introduce mainly a gas component of exhaust gas into the gas separation chamber 119 through outer introduction holes 115 of the after-mentioned outer protector 110, into the inner protector 120; i.e., into a gas detection chamber 129 to which the detecting portion 11 of the detecting element 10 is exposed. A front end portion of the circumferential wall 122 of the inner protector 120 has drain holes 150 which are arranged at a plurality of (six in the present embodiment) circumferential positions. The drain holes 150 are each formed in such manner that an L-shaped cut portion is pressed toward the interior of the gas detection chamber 129. The drain holes 150 are adapted to lead water (water droplets) and the like contained in exhaust gas which is introduced into the gas separation chamber 119, to the exterior of the gas sensor via the gas detection chamber 129. The drain holes 150 are located frontward of the inner introduction holes 130. The front end wall 124 of the inner protector 120 has an exhaust hole 160 for exhausting exhaust gas and water droplets which have been introduced into the gas detection chamber 129, to the exterior of the gas sensor.

The front end wall 124 of the inner protector 120 has a recess portion 125, which is formed in such manner as to externally press a portion of the front end wall 124 toward the interior of the inner protector 120 and is thus recessed toward the detecting element 10. The recess portion 125 assumes a concave shape such that a side wall 127 surrounds the peripheral edge of a bottom wall 126. The exhaust hole 160 is opened in such manner as to extend through a portion of the side wall 127. By virtue of this configuration, even when a water droplet or the like enters the recess portion 125 from outside the inner protector 120 along the direction of the axis O, the water droplet is obstructed by the bottom wall 126 and is thus unlikely to reach the detecting element 10. Therefore, the detecting element 10 can be protected from contact with adhering water droplets. Furthermore, the recess portion 125 is located frontward of the rear end of the taper portion 123 (i.e., the boundary between the taper portion 123 and the circumferential wall 122), thereby increasing the distance between the front end of the detecting element 10 and the bottom wall 126 of the recess portion 125 with respect to the direction of the axis O. Thus, even when a portion of water droplets having entered the recess portion 125 and having collided with the bottom wall 126 pass through the exhaust hole 160 and enter the gas detection chamber 129, such a water splash is unlikely to reach the detecting element 10. Therefore, the detecting element 10 can be protected from contact with adhering water droplets.

The exhaust hole 160 is located frontward of the rear end of the drain hole 150. In other words, in forming the recess portion 125, the recess portion 125 is pressed inward such that the bottom wall 126 is not located rearward of the rear end of the drain hole 150. By virtue of this configuration, with respect to a flow path of exhaust gas flowing in the outer and inner protectors 110 and 120, the exhaust hole 160 is located downstream of the drain holes 150. This prevents backward entry of a water droplet which has been introduced into the gas detection chamber 129 through the drain hole 150, into the gas separation chamber 119 through the drain hole 150.

In the present embodiment, the exhaust hole 160 is opened in each of two facing regions of the side wall 127 (in FIG. 2, left and right end regions of the side wall 127) of the recess portion 125. Each of the exhaust holes 160 has an opening which has a trapezoidal shape such that a front end width (a length as measured on a side toward the front end wall 124 in a direction orthogonal to the axis O) of the opening is greater than a rear end width (a width on a side toward the bottom wall 126) of the opening. Therefore, the opening area of a single exhaust hole can be increased. Also, the opening area of each exhaust hole 160 can be increased without the need to increase the depth of the recess portion 125. As a result, this configuration can enhance exhaust-gas exhaustibility and water-droplet drainage from the exhaust holes 160 of the inner protector 120.

The inner protector 120 is fixed to the metallic shell 50 such that a facing direction of the two exhaust holes 160 coincides with a thickness direction (a left-right direction in FIGS. 2A and 2B, a direction perpendicular to the paper on which FIG. 3A appears, and a vertical direction in FIG. 3B) of the detecting element 10, which assumes the form of a plate and whose detecting portion 11 is accommodated in the gas detection chamber 129. Particularly, as shown in FIG. 2B and FIG. 3B, the detecting element 10 and the exhaust holes 160 are arranged in such manner as to not overlap one another with respect to the direction of the axis O. That is, the detecting element 10 is not located on a straight line which extends between the interior and the exterior of the inner protector 120 through the exhaust hole 160. More specifically, the detecting element 10 can not be viewed through the exhaust hole 160 from outside the inner protector 120. By virtue of this configuration, even when a water droplet enters the recess portion 125 from outside the inner protector 120 along a direction different from the direction of the axis O and then enters the inner protector 120 through the exhaust hole 160, the water droplet does not come in contact with the detecting element 10. Thus, the detecting element 10 can be protected from contact with adhering water droplets.

If, as mentioned above, the exhaust holes 160 and the detecting element 10 are arranged in such manner as to not overlap one another with respect to the direction of the axis O, even though the thickness direction of the detecting element 10 and the facing direction of the two exhaust holes 160 do not entirely coincide with one another, the detecting element 10 can be sufficiently protected from contact with adhering water droplets. For example, the detecting element 10 may be held in the metallic shell 50 such that the axial direction (extending direction) of the detecting element 10 is inclined relative to the axis O, or the thickness direction of the detecting element 10 and the facing direction of the two exhaust holes 160 may deviate from one another around the axis O. That is, if the detecting element 10 is invisible when the interior of the gas detection chamber 129 is viewed from the outside through the exhaust hole 160, a water droplet which has entered the gas detection chamber 129 from the outside through the exhaust hole 160 is unlikely to reach the detecting element 10. Therefore, the detecting element 10 can be protected from contact with adhering water droplets.

The recess portion 125 is formed on the front end wall 124 such that its center coincides with the axis O and such that the bottom wall 126 of the recess portion 125 is located frontward of the detecting element 10 with respect to the direction of the axis O. The bottom wall 126 of the recess portion 125 is located frontward, with respect to the direction of the axis O, of the rear end of each drain hole 150 opened in the circumferential wall 122 of the inner protector 120. Thus, the exhaust holes 160 are located frontward of the rear end of each drain hole 150 with respect to the direction of the axis O. This configuration prevents backward entry of a water droplet which has been introduced into the inner protector 120, into the gas separation chamber 119 between the outer protector 110 and the inner protector 120 through the drain hole 150. This structure prevents water from remaining within the protector 100, thereby enhancing drainage from inside the inner protector 120 and thus protecting the detecting element 10 from contact with adhering water.

A rear end portion 111 of the outer protector 110 is fitted to the outer circumference of the open end portion 121 of the inner protector 120. Spot-welding is performed on the outer circumference of the rear end portion 111 of the outer protector 110, whereby the outer protector 110 is fixed to the inner protector 120 while the rear end portion 111 of the outer protector 110 is superposed on the open end portion 121 of the inner protector 120. Notably, the outer protector 110 may be laser-welded to the inner protector 120. A front end portion 113 of the outer protector 110 is bent inward toward the outer circumferential surface of the circumferential wall 122 of the inner protector 120 in the vicinity of the taper portion 123 of the inner protector 120. This closes a front end of a clearance between the outer circumferential surface of the inner protector 120 and the inner circumferential surface of the outer protector 110, whereby the clearance serves as the above-mentioned gas separation chamber 119. The taper portion 123 of the inner protector 120 projects frontward from the front end portion 113 of the outer protector 110 with respect to the direction of the axis O, thereby being exposed to the exterior of the gas sensor. As mentioned above, the recess portion 125 is located frontward of the rear end of the taper portion 123. Accordingly, the recess portion 125 is located frontward of the front end portion 113 of the outer protector 110. Accordingly, the exhaust holes 160 are located at a furthermost downstream position with respect to a flow path of exhaust gas and a water droplet which flow in the protector 100. Therefore, exhaust-gas exhaustibility and water-droplet drainage from the exhaust holes 160 can be further enhanced.

A front end portion of the circumferential wall 112 of the outer protector 110 has a plurality of (six in the present embodiment) outer introduction holes 115 which are arranged circumferentially at a position located frontward of the inner introduction holes 130 of the inner protector 120 and which are adapted to establish communication between the gas separation chamber 119 and the exterior of the outer protector 110. Each of the outer introduction holes 115 has a guide portion 116 which extends inward. The guide portions 116 cause exhaust gas, which is externally introduced into the gas separation chamber 119 through the outer introduction holes 115, to swirl around the outer circumferential surface of the circumferential wall 122 of the inner protector 120. Furthermore, with respect to the direction of the axis O, the front end of the detecting element 10 is located rearward of the rear end of each of the outer introduction holes 115 of the outer protector 110. Also, the drain holes 150 of the inner protector 120 are located frontward of the rear end of each of the outer introduction holes 115. That is, in a case where a water droplet or the like which flies toward the circumferential wall 112 of the outer protector 110 from the outside enters the gas separation chamber 119 through the outer introduction hole 115 and directly passes through the drain hole 150 to thereby enter the gas detection chamber 129, the front end of the detecting element 10 is not located in a direction of entry of the water droplet or the like. By virtue of this configuration, a water droplet or the like which has come flying from the outside does not come in direct contact with the detecting element 10 and is drained to the exterior of the gas sensor through the exhaust hole 160, so that the detecting element 10 can be protected from contact with adhering water.

When the thus-configured gas sensor 1 is attached to an exhaust pipe of an internal combustion engine, a front end portion of the gas sensor 1 which extends frontward from the externally threaded portion 51 is exposed to the interior of the exhaust pipe. Exhaust gas which flows through the exhaust pipe collides with the protector 100 from at least a direction different from the direction of the axis O (for example, from a direction orthogonal to the axis O) and is introduced into the gas separation chamber 119 through the outer introduction holes 115 of the outer protector 110. At this time, the flow direction of exhaust gas is guided by the guide portions 116 such that exhaust gas swirls in the gas separation chamber 119 along the outer circumferential surface of the circumferential wall 122 of the inner protector 120. Inertial force associated with the swirl separates a gas component and water contained in exhaust gas from one another, water having a higher specific gravity than the gas component. Water having a high specific gravity is introduced into the gas detection chamber 129 of the inner protector 120 through the drain holes 150, whereas the gas component is introduced into the gas detection chamber 129 through the inner introduction hole 130. By means of contact between the detecting portion 11 of the detecting element 10 and the gas component of exhaust gas introduced into the gas detection chamber 129, the gas sensor 1 detects the concentration of oxygen contained in exhaust gas. Meanwhile, when exhaust gas which flows through the exhaust pipe collides with the taper portion 123 of the inner protector 120, a gas flow arises toward the front end wall 124 along the taper. This gas flow generates a negative pressure (suction) in the vicinity of the recess portion 125. Thus, exhaust gas and water droplets within the gas detection chamber 129 are sucked out to the exterior of the gas sensor through the exhaust holes 160. In this manner, a flow path of exhaust gas flowing in the protector 100 is established.

The above-mentioned exhaust holes 160 can be formed as follows: a portion of the front end wall 124 is pressed into the gas detection chamber 129 to thereby form the recess portion 125; subsequently, respective openings are formed in the side wall 127. However, the exhaust holes 160 can be formed in a simpler procedure. For example, two parallel slits are formed in the front end wall 124, and then a central portion between the slits is pressed into the gas detection chamber 129, thereby forming the recess portion 125. The central portion between the slits serves as the bottom wall 126 of the recess portion 125; opposite end portions of the central portion between the slits collectively serve as the side wall 127; and the slits are formed into the respective exhaust holes 160.

Figure 4A:
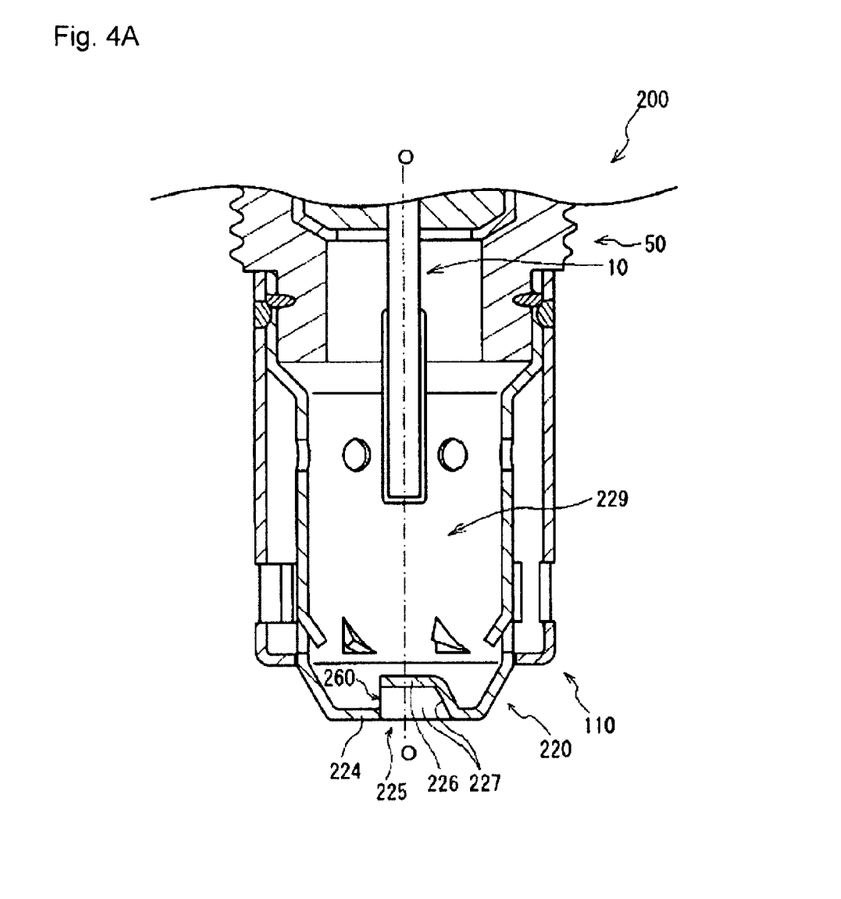
FIG. 4A is a side view.
Figure 4B:
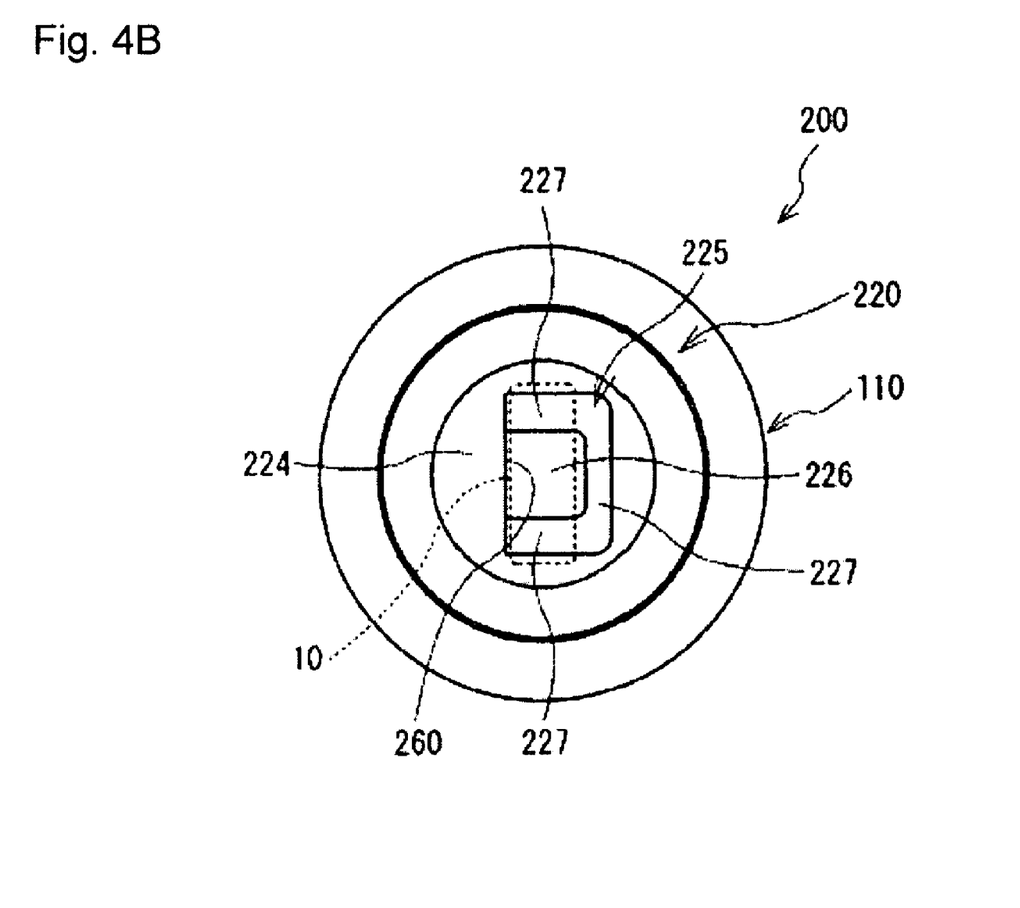
FIG. 4B is a view from the front-end side.

The present invention is not limited to the above-described embodiment, but may be modified in various forms. For example, the recess portion 125 of the present embodiment is formed by pressing a central portion between two parallel slits formed in the front end wall 124 toward the interior of the inner protector 120. However, as in the case of a gas sensor 200 shown in FIGS. 4A and 4B, the following method may be employed: a single slit is formed in a front end wall 224, and then a portion on one side of the slit is pressed into a gas detection chamber 229 of an inner protector 220, thereby forming a recess portion 225 which is recessed toward the detecting element 10. In this case, the interior of the recess portion 225 is surrounded around the axis O from three directions by a side wall 227, and an exhaust hole 260 is opened in the remaining one direction. A bottom wall 226 can sufficiently protect the detecting element 10 against exposure to the exterior of the gas sensor. Also, in this case, the inner protector 220 is fixed to the metallic shell 50 while, as shown in FIG. 4B, the detecting element 10 and the exhaust hole 260 are arranged so as to not overlap one another with respect to the direction of the axis O. That is, the detecting element 10 and the exhaust hole 260 are arranged such that, when the interior of the inner protector 220 is viewed from the outside through the exhaust hole, the detecting element 10 is not visible. By virtue of this configuration, even when a water droplet which has come flying from the outside enters the inner protector 220 through the exhaust hole 260, the water droplet does not come in contact with the detecting element 10. Thus, the detecting element 10 can be protected from contact with adhering water droplets. Of course, three or more exhaust holes may be provided. The recess portion may be formed without providing a slit. In this case, in a subsequent step, an opening is formed in the side wall of the thus-formed recess portion.

In the protector 100 of the present embodiment shown in FIGS. 2 and 3, the drain hole 150 and the inner introduction hole 130 are formed on the same generatrix of the circumferential wall 122 of the inner protector 120, and the outer introduction hole 115 is formed on a generatrix of the outer protector 110 which is located in the same radial direction as that of the generatrix of the inner protector 120 on which the drain hole 150 and the inner introduction hole 130 are formed. However, the drain hole 150 and the inner introduction hole 130 may be formed on different generatrices, and the outer introduction hole 115 may be formed on a generatrix located in a radial direction different from those of the generatrices on which the drain hole 150 and the inner introduction hole 130 are formed. Alternatively, the drain hole 150 and the inner introduction hole 130 may be formed on different generatrices, whereas the outer introduction hole 115 may be formed on a generatrix located in the same radial direction as that of one of the generatrices. Further, alternatively, the drain hole 150 and the inner introduction hole 130 may be formed on the same generatrix, whereas the outer introduction hole 115 may be formed on a generatrix located in a radial direction different from that of the generatrix on which the drain hole 150 and the inner introduction hole 130 are formed. The number of the outer introduction holes 115, that of the drain holes 150, and that of the inner introduction holes 130 are not limited to six. Also, their size can be determined without particular limitation so long as the objectives of the invention are met.

Figure 5:
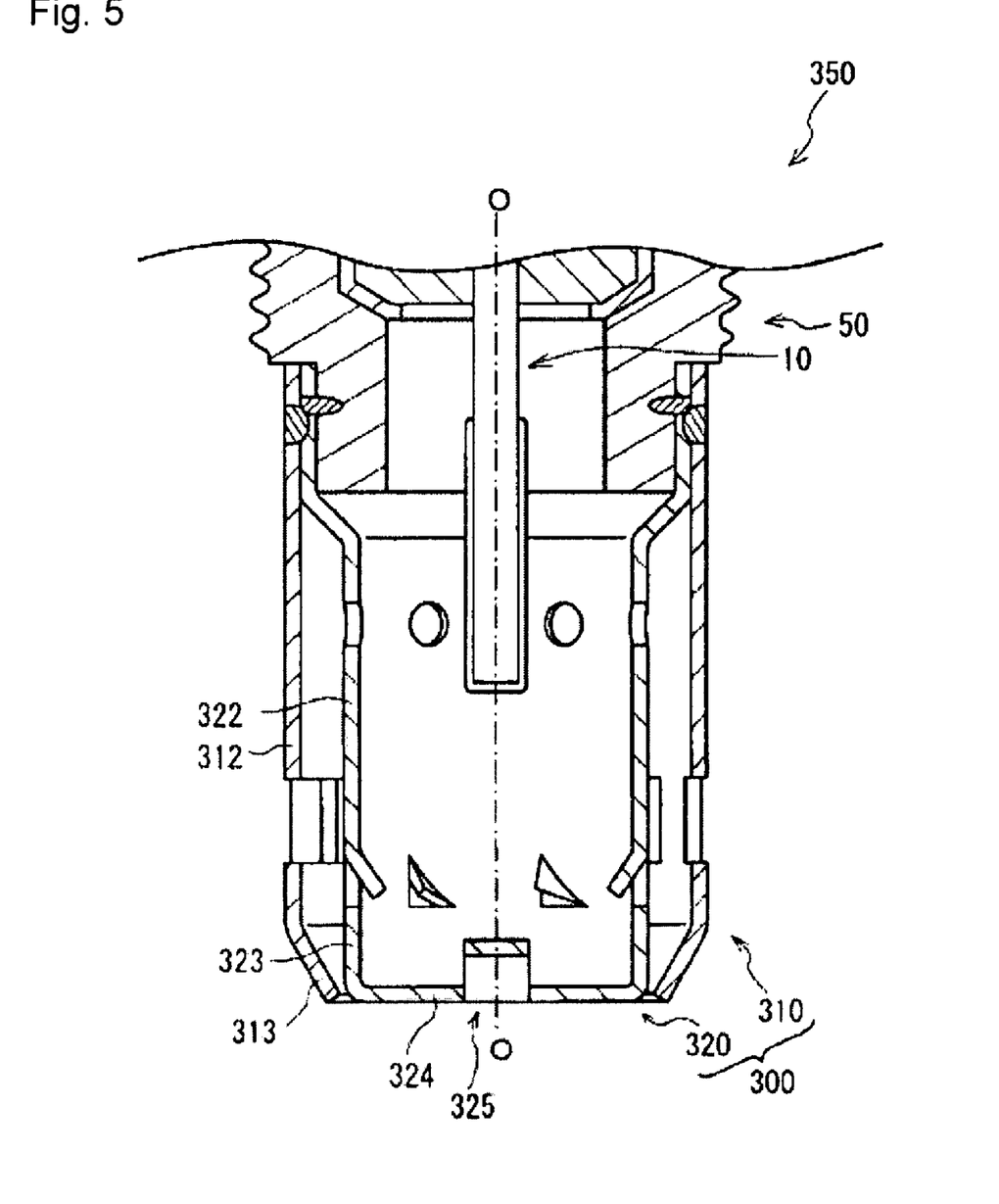
FIG. 5 is a sectional view showing a protector 300 of a gas sensor 350 as a variant of the gas sensor 1.

According to the present embodiment, the taper portion 123 is formed on the front end side of the circumferential wall 122 of the inner protector 120 and in such manner as to reduce in diameter toward the front end wall 124. However, such a taper portion may be formed on the front end side of the outer protector 110. For example, as in the case of an outer protector 310 of a gas sensor 350 shown in FIG. 5, a taper portion 313 may be formed on the front end side of a circumferential wall 312 of the outer protector 310 and in such manner as to reduce in diameter toward a front end wall 324 of an inner protector 320. Even in a thus-configured protector 300, as in the case of the protector 100 of the present embodiment, when exhaust gas which flows through an exhaust pipe collides with the taper portion 313 of the outer protector 310, a gas flow arises toward the front end wall 324 of the inner protector 320 along the taper portion 313. This gas flow generates a negative pressure (suction) in the vicinity of a recess portion 325. In this case, as shown in FIG. 5, the outer protector 310 is configured such that the front end of the taper portion 313 of the outer protector 310 is substantially flush with the front end wall 324 of the inner protector 320. The inner protector 320 is configured such that a portion 323 of the inner protector 320 is not tapered, but extends straight axially from a circumferential wall 322. This configuration is preferred since a substantially continuous surface can be formed from the taper portion 313 to the front end wall 324 for smoothly guiding exhaust gas toward the front end wall 324. Of course, although unillustrated, both the outer protector and the inner protector may have respective taper portions. In this case, preferably, the taper portion of the outer protector is made continuous with the taper portion of the inner protector so as to smoothly guide exhaust gas toward the front end wall of the inner protector along the both taper portions.

INDUSTRIAL APPLICABILITY

The present invention can be similarly applied to protectors for use in oxygen sensors, $NO_x$ sensors, HC sensors, temperature sensors, and the like.

It should further be apparent to those skilled in the art that various changes in form and detail of the invention as shown and described above may be made. It is intended that such changes be included within the spirit and scope of the claims appended hereto.

This application is based on Japanese Patent Application No. 2006-250097 filed Sep. 14, 2006 and Japanese Patent Application No. 2007-114357 filed Apr. 24, 2007, incorporated herein by reference in their entirety.

What is claimed is:

1. A gas sensor comprising:
   a detecting element which extends in an axial direction and has a detecting portion at a front end portion thereof, the detecting portion detecting a specific gas component contained in a gas-to-be-measured;
   a housing which holds and radially encloses the detecting element, the detecting portion of the detecting element projecting from a front end portion of the housing;
   an inner protector which has a circumferential wall, said inner protector having a front end wall located on a front side of the circumferential wall, and a rear, open end portion fixed to a front end portion of the housing so as to accommodate the detecting portion of the detecting element in the inner protector, and which inner protector has an inner introduction hole formed in its circumferential wall for introducing the gas-to-be-measured into the inner protector; and
   an outer protector which assumes a cylindrical shape enclosing the circumferential wall of the inner protector, such that a clearance is present between the inner protector and the outer protector, and which outer protector has an outer introduction hole formed in a circumferential wall of the outer protector for introducing the gas-to-be-measured into the clearance;
   wherein at least either the inner protector or the outer protector has a taper portion formed on a front end side of its circumferential wall and reducing frontward in outside diameter, and
   the front end wall of the inner protector includes a recess portion having:
      a bottom wall located closer to the detecting element than the front end wall;
      a side wall connecting the front end wall and the bottom wall; and
      an exhaust hole formed in the side wall adapted to exhaust the gas-to-be-measured.

2. The gas sensor according to claim 1, wherein the circumferential wall of the inner protector has a drain hole located frontward of the inner introduction hole for introducing into the inner protector a water droplet which has entered the clearance; and the exhaust hole of the recess portion is located frontward of a rear end of the drain hole.

3. The gas sensor according to claim 1, wherein the detecting element assumes the form of a plate, and the exhaust hole does not overlap the detecting element in the axial direction.

4. The gas sensor according to claim 1, wherein the exhaust hole is opened in the form of a through-hole in each of two facing regions of the side wall of the recess portion.

5. The gas sensor according to claim 4, wherein the detecting element assumes the form of a plate, and the inner protector is fixed to the housing such that a facing direction of the two exhaust holes of the recess portion coincides with a thickness direction of the detecting element held by the housing.

6. The gas sensor according to claim 1, wherein the recess portion is located frontward of a rear end of the taper portion.

7. The gas sensor according to claim 1, wherein the exhaust hole has an opening which has a trapezoidal shape such that a front end width of the opening is greater than a rear end width of the opening.

8. The gas sensor according to claim 1, wherein the drain hole is located frontward of a rear end of the outer introduction hole of the outer protector, and a front end of the detecting element is located rearward of the rear end of the outer introduction hole of the outer protector.

9. The gas sensor according to claim 1, wherein the taper portion is present on the inner protector, and the inner protector projects from a front end of the outer protector such that the bottom wall of the recess portion is located frontward of the front end of the outer protector.

10. The gas sensor according to claim 1, wherein the detecting element is configured so that the detecting element cannot be viewed through the exhaust hole from outside the inner protector.

11. A gas sensor comprising:

a detecting element which extends in an axial direction and has a detecting portion at a front end portion thereof, the detecting portion detecting a specific gas component contained in a gas-to-be-measured;

a housing which holds and radially encloses the detecting element, the detecting portion of the detecting element projecting from a front end portion of the housing;

an inner protector which has a circumferential wall, said inner protector having a front end wall located on a front side of the circumferential wall, and a rear end portion fixed to a front end portion of the housing so as to accommodate the detecting portion of the detecting element in the inner protector, and which inner protector has an inner introduction hole formed in its circumferential wall for introducing the gas-to-be-measured into the inner protector and an exhaust hole formed in its front end wall adapted to exhaust the gas-to-be-measured; and an outer protector which has a circumferential wall enclosing the circumferential wall of the inner protector with a clearance between the circumferential wall of the inner protector and the circumferential wall the outer protector, and which outer protector has an outer introduction hole formed in the circumferential wall of the outer protector for introducing the gas-to-be-measured into the clearance;

wherein the entirety of the front end wall of the inner protector is exposed and not covered by the outer protector, and the exhaust hole is configured such that the detecting element cannot be viewed in the axial direction through the exhaust hole from outside the inner protector.

12. The gas sensor according to claim 11, wherein the front end wall of the inner protector includes a recessed portion having a bottom wall located closer to the detecting element than the front end wall; a side wall connecting the front end wall and the bottom wall; and an exhaust hole formed in the side wall adapted to exhaust the gas-to-be-measured.

* * * * *